United States Patent [19]

Montgomery et al.

[11] Patent Number: 5,034,518

[45] Date of Patent: Jul. 23, 1991

[54] 2-FLUORO-9-(2-DEOXY-2-FLUORO-β-D-ARABINOFURANOSYL) ADENINE NUCLEOSIDES

[75] Inventors: John A. Montgomery; John A. Secrist, III, both of Birmingham, Ala.

[73] Assignee: Southern Research Institute, Birmingham, Ala.

[21] Appl. No.: 355,358

[22] Filed: May 23, 1989

[51] Int. Cl.$^5$ .................. C07H 19/19; C07H 19/16
[52] U.S. Cl. ........................................ 536/26; 536/24
[58] Field of Search ................................ 536/24, 26

[56] References Cited

U.S. PATENT DOCUMENTS

| | | | |
|---|---|---|---|
| 4,188,378 | 2/1980 | Montgomery | 536/26 |
| 4,210,745 | 7/1980 | Montgomery | 536/24 |
| 4,357,324 | 11/1982 | Montgomery et al. | 536/26 |
| 4,751,221 | 6/1988 | Watanabe et al. | 514/46 |
| 4,918,179 | 4/1990 | Watanabe et al. | 536/24 |

OTHER PUBLICATIONS

*Journal of Medicinal Chemistry,* 1986, vol. 29, No. 11, pp. 2389-2392, Montgomery et al.
Secrist, III et al., *J. Med. Chem.* 1988, 31, 405.
Doskocil and Holy, *Coll. Czech. Chem. Commun.,* 1977, 42, 370.
Haertle et al., (1988) J. Biol. Chem., vol. 253 (12): 5870-5875.
Struck et al., (1982) Biochem. Pharm., vol. 31, No. 11, pp. 1975-1978.
Huang et al., (1987) Biochem Pharm., vol. 36, No. 7, pp. 2945-2954.

*Primary Examiner*—Johnnie R. Brown
*Assistant Examiner*—Gary L. Kunz
*Attorney, Agent, or Firm*—Roylance, Abrams, Berdo & Goodman

[57] ABSTRACT

There are disclosed nucleosides having Formula I:

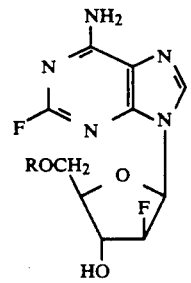

wherein R is H or acyl. These compounds have anticancer activity.

2 Claims, No Drawings

2-FLUORO-9-(2-DEOXY-2-FLUORO-β-D-ARABINOFURANOSYL) ADENINE NUCLEOSIDES

BACKGROUND OF THE INVENTION

This invention relates to certain 2'-F, 2-halo substituted purine nucleosides.

Certain arabinofuranosyl nucleosides have well known antiviral (araA) and anticancer (araC) activity. Some arabinofuranosyl nucleosides with 2'-substituents other than a hydroxyl also have shown useful biological effects. All of these nucleosides require activation (phosphorylation) to be effective, and generally this is accomplished by different enzyme than the corresponding ribofuranosyl nucleosides.

U.S. Pat. No. 4,751,221 to Watanabe et al discloses nucleosides represented by the following formula:

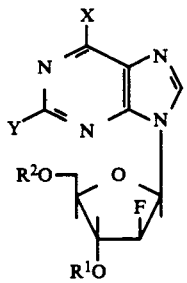

wherein

X and Y are the same or different and are hydrogen, $OR^3$ (keto or enol), $SR^3$, $NR^3R^4$, NH acyl or halogen such as chlorine or bromine;

$R^3$ and $R^4$ are the same or different and are hydrogen, lower alkyl of 1 to 7 carbon atoms such as methyl, ethyl, propyl and the like, aralkyl such as benzyl, benzhydryl, p-methoxybenzyl and the like, or aryl such as phenyl, p-chlorophenyl, toluyl, p-methoxyphenyl, naphthyl and the like;

NH acyl may be an alkanoyl or aroyl amide; and $R^1$ and $R^2$ are the same or different hydrogen or acyl groups which may be alkanoyl groups of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoleyl, oleyl, linolenyl, arachidonyl and the like.

Montgomery et al, *Journal of Medicinal Chemistry* 1986, Vol. 29, No. 11, pps. 2389-2392 disclose nucleosides having the following formula:

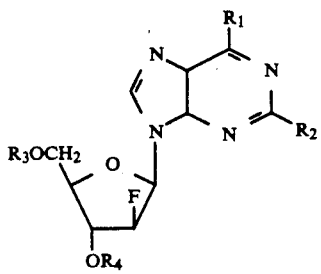

wherein $R^1$ and $R^2$ are the same and may be Cl or $NH_2$, $R_3$ may be benzoyl or hydrogen, and $R_4$ may be acetyl or hydrogen.

SUMMARY OF THE INVENTION

It has been found that incorporating a 2-halo substituent onto the purine ring significantly alters the metabolism of adenine nucleosides, specifically by reducing the ability of the compound to serve as a substrate for adenosine deaminase; that substituting a fluorine in the arabino configuration at C-2' makes these derivatives highly resistant to phosphorolytic cleavage; and that the combination of these two fractions in the same molecule provide anticancer activity.

Thus, in accordance with this invention, there are provided nucleosides represented by Formula I

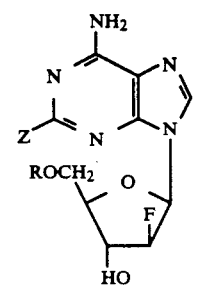

wherein Z is F, Cl, or Br, and R is hydrogen or acyl. When R is acyl, the derivatives act as prodrugs in prolonging the in vivo life of the parent drug.

The compounds of this invention are useful in the treatment of cancer, e.g., chronic lymphocytic leukemia.

DETAILED DESCRIPTION OF THE INVENTION

In the following discussion, reference will be made to the following Formula 1. The examples include descriptions of compounds designated 1a–1g wherein the various substituents in these compounds are defined following Formula 1.

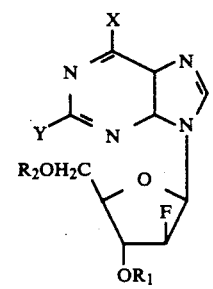

a) $X=Y=Br$; $R_1=Ac$; $R_2=Bz$
b) $X=NH_2$; $Y=Br$; $R_1=R_2=H$
c) $X=Y=Cl$; $R_1=Ac$; $R_2=Bz$
d) $X=NH_2$; $Y=Cl$; $R_1=R_2=H$
e) $X=Y=NH_2$; $R_1=Ac$; $R_2=Bz$
f) $X=NH_2$; $Y=F$; $R_1=Ac$; $R_2=Bz$
g) $X=NH_2$; $Y=F$; $R_1=R_2=H$

In the definition of these substituents, "Bz" stands for benzoyl and "Ac" stands for acetyl.

The following examples illustrate the preparation of the compounds of Formula 1.

EXAMPLE 1

2,6-Dibromo-9-(3-O-acetyl-5-O-benzyl-2-deoxy-2-fluoro-$\beta$-D-arabinofuranosyl)-9H-purine (1a)

A solution of 3-acetyl-5-benzoyl-2-deoxy-2-fluoroarabinofuranosylbromide (33.2 mmol) in 400 mL of dry dichloroethane was stirred for 10 minutes with 4A molecular sieve (250 mL) before the addition of (9.3 g, 33.5 mmol) 2,6-dibromopurine. The mixture was vigorously stirred with an overhead stirrer and placed in a preheated 100° C. oil bath. Heating was continued for 32 hours until all the bromosugar was consumed. (TLC 2:1 cyclohexane-ethyl acetate, using 4-(4-nitrobenzyl) pyridine spray for detection). After the mixture had cooled to room temperature, it was filtered through Celite. The solids were washed with dichloroethane, and the combined filtrates were evaporated to dryness in vacuo. The residue (16.5 g) was a mixture of three nucleosides which were separated by flash chromatography on 150 g of silica gel (230-400 mesh) using 2:1 cyclohexane-ethyl acetate as the eluting solvent. By combining pure fractions, the desired compound was obtained as a glass 3.64 g (19.7%) which was chromatographically homogeneous, but would not crystallize. A second column run on impure fractions gave 2.21 g (11.9%) more pure product for a total yield of 31.6%. MS 557 (M+1)+. Anal. Calcd. for $C_{19}H_{15}Br_2FN_4O_5 \cdot 0.2C_6H_{12}$: C, 42.19; H, 3.05; N, 9.74. Found C, 42.11; H, 3.10; N, 9.35.

EXAMPLE 2

2-Bromo-9-(2-deoxy-2-fluoro-$\beta$-D-arabinofuranosyl)-9H-purin-6-amine (1b)

A solution of 1a (5.84 g, 10.5 mmol) in 400 mL of ethanolic ammonia (saturated at 0° C.) was sealed in a glass-lined stainless steel bomb and left at room temperature for 3 days. The solution was evaporated to dryness and evaporated with ethanol to remove ammonia. The residue, containing the desired product and 5'-benzoyl compound, was dissolved in 440 mL of acetonitrile and 120 mL of water. Lithium hydroxide monohydrate (881 mg, 21 mmol) was added, and the solution was stirred for 16 hours at room temperature. Thin-layer chromatography (5:1 CHCl$_3$-MeOH) indicated complete reaction. The chilled solution was carefully neutralized with glacial acetic acid and evaporated to dryness. The white solid residue was recrystallized from water. The product was dried in vacuo at room temperature at 100° C. for 2 hours: 2.15 g (59.2%). Mp 209-210° C., TLC 5:1 CHCl$_3$-MeOH R$_f$ 0.47; HPLC 99.8% 9:1; H$_2$O-MeCN; MS, 3.48 (M+1)+; UV $\lambda$max pH 1 264 (14.3), pH 7 264 (14.9), pH 13 264 (15.2). Anal. Calcd. for $C_{10}H_{11}BrFN_5O_3$: C, 34.50; H, 3.18; N, 20.12. Found: C, 34.36; H, 3.28; N, 19.93.

EXAMPLE 3

2-Chloro-9-(2-deoxy-2-fluoro-$\beta$-D-arabinofuranosyl)-9H-purin-6-amine (1d)

A solution of 1c prepared by the procedure described by Montgomery et al, *Journal of Medicinal Chemistry*, 1986, Vol. 29, No. 11, pps. 2389-2392, (5.1 g, 10.9 mmol) in ethanol saturated (0° C.) with anhydrous ammonia (100 mL), was placed in a glass-lined stainless steel bomb and left at room temperature for three days. TLC (2:1 cyclohexane-ethyl acetate and 5:1 CHCl$_3$-MeOH indicated the absence of starting material. However, two major products were present, the desired compound and its 5'-benzoyl analog. The solution was evaporated to dryness and co-evaporated with acetonitrile. The residue was dissolved in acetonitrile (100 mL) and diluted with water (60 mL) before the addition of lithium hydroxide monohydrate (915 mg, 21.8 mmol). The solution was stirred at room temperature for 3 hours, at which time TLC (5:1 CHCl$_3$-MeOH) indicated complete reaction. The solution was cooled, neutralized with acetic acid and evaporated to dryness. Three recrystallizations from water gave the pure compound: 14. g (42.3%). Mp 225-226° C.; TLC 5:1 CHCl$_3$-MeOH, R$_f$ 0.40; HPLC 99% 4:1 H$_2$O-MeCN; Ms, z/e 304 (M+1)+; UV $\lambda$max 263 (15.5) at pH 1; 263 (16.2) at pH 7; 263 (16.4) at pH 13. Anal. Calcd. for $C_{10}H_{11}ClFN_5O_3 \cdot H_2O$: C, 37.34; H, 4.07; N, 21.77. Found: C, 37.62; H, 3.98; N, 21.88.

EXAMPLE 4

2-Fluoro-9-(3-O-acetyl-5-O-benzoyl-2-deoxy-2-fluoro-$\beta$-D-arabinofuranosyl)-9H-purin-6-amine (1f)

Diamino compound is prepared by the procedure described by Montgomery et al, *Journal of Medicinal Chemistry*, 1986, Vol. 29, No. 11, pps. 2389-2392, (700 mg, 1.63 mmol) was dissolved in 3:2 HF-pyridine (15 mL) at −25° C. and treated with tert-butylnitrile (271 $\mu$l, 2.28 mmol). After 1 hour at −20° C., the reaction was incomplete as indicated by TLC. More tert-butyl nitrite (70 $\mu$l, 0.59 mmol) was added, and the reaction was held at −20° C. for an additional 2 hours. The cold reaction solution was added dropwise to saturated aqueous NaHCO$_3$ (1 mL) containing ice. The foaming mixture was stirred vigorously for 20 minutes, then diluted with CHCl$_3$ (300 mL). The layers were separated, and the aqueous layer was extracted with more CHCl$_3$ (2×175 mL). The combined organic extracts were washed with water (3×175 mL), dried (MgSO$_4$), and evaporated to dryness. This residue in CHCl$_3$ was applied to a flash column containing 50 g of silica gel (230-400 mesh) with CHCl$_3$ as eluant. Fractions were combined to give essentially pure 1f, 500 mg (70%). Crystallization of a small sample from EtOH gave pure (1f). Mp 208-209° C.; TLC 95:5 CHCl$_3$-MeOH, R$_f$ 0.45; HPLC 99%, 1:1 H$_2$O-MeCN; MS, z/e 434 (M+1)+. Anal. Calcd. for $C_{19}H_{17}F_2N_5O_5$: C, 52.66; H, 3.95; N, 16.16. Found: C, 52.48; H, 3.92; N, 15.98.

EXAMPLE 5

2-Fluoro-9-(2-deoxy-2-fluoro-$\beta$-D-arabinofuranosyl)-9-H-purin-6-amine (1g)

A suspension of 1f (430 mg, 0.99 mmol) in 1:1 MeCN-H$_2$O (40 mL) was treated in one portion with solid lithium hydroxide monohydrate (125 mg, 2.97 mmol). The reaction became a clear solution after being stirred at room temperature for 20 minutes. A 3-h TLC aliquot showed the deblocking to be Glacial acetic acid (57 $\mu$l) was added, and the solution was evaporated until white solid deposited. After being chilled, the solid was collected, washed with cold water, and dried in vacuo at room temperature to give crude 1g, 252 mg. This solid was dissolved in 40 mL of water and applied to a water-equilibrated SM-4 Bio-Bead column (1.5×32 cm). After initial elution with water, the product was eluted with a stepwise gradient, 5% →20% EtOH in water. The residue from the combined, evaporated column fractions was crystallized from 25 mL of boiling water with charcoal treatment and dried in vacuo at 56° C. for 16 hours to give pure 1g: 178 mg (59%). Mp 207°-209° C.; TLC 5:1 CHCl$_3$-MeOH, R$_f$ 0.50; HPLC 99%, 9:1 H$_2$O-MeCN; MS, z/e 288 (M+1)+; UV λ max pH 1 261 (14.0), 268 (sh), pH 7 260 (15.1), 268 (sh), pH 13 261 (14.9), 268 (sh). Anal. Calcd. for C$_{10}$H$_{11}$F$_2$N$_5$O$_3$·H$_2$O: C, 39.35; H, 4.29; N, 22.94. Found: C, 39.51; H, 4.21; N, 22.94.

If rapid clearance is a problem, then it may be desirable to prepare the 5'-O-acyl derivatives of the compounds of Examples 2, 3 and 5. Such 5'-O-acyl derivatives are prodrugs that have increased activity on the basis of an increased half-life in living systems, allowing delivery of more active drug to the target site. A general experimental procedure for 5-acylation is as follows.

EXAMPLE 6

A solution of dry 2-halo-9-(2-deoxy-2-fluoro-β-D-arabinofuranosyl)adenine (1 mmol) in 10 mL of 1:1 pyridine-N,N-dimethylformamide was cooled to 0° C. and treated dropwise with the appropriate acyl chloride (1.25 mmol). After 6 hours at 0° C., the solution was poured into ice water (100 mL), stirred 15 minutes, and refrigerated overnight. If a white solid precipitated, it was collected, washed with cold water, and dried in vacuo at room temperature to give the crude 5'-acylated nucleoside. If no precipitate formed, the reaction mixture was extracted with CHCl$_3$ (4×25 mL). The combined extracts were dried (MgSO$_4$) and evaporated to give the crude 5'-acylated nucleoside as a glass. If needed, the crude product was purified by silica gel chromatography on a flash column or thick plate with 9:1 CHCl$_3$-MeOH as eluant. Pure 5'-acylated nucleoside was obtained as a crystalline solid from an appropriate recrystallization solvent such as acetonitrile, diethyl ether, or toluene-acetonitrile.

EXAMPLE 7

Comparison of Cytotoxicity

Table 1 sets forth the results of cytotoxicity tests. For L1210 cells, CCRF-CEM cells, and K562 cells, the IC$_{50}$ is the concentration required to decrease cellular proliferation by 50% as compared to untreated controls. The cells were grown in suspension cultures and the number of cells present was determined at 24, 48 and 72 hours. The values shown in Table 1 are 48 hour values for L1210 cells and 72 hour values for CCRF-CEM cells and K562 cells.

For H.Ep.-2 cells, the IC$_{50}$ is the concentration required to reduce colony formation by 50% as compared to controls. One hundred cells in 10 mL of medium were placed in prescription bottles, and after 10 days incubation, the medium was decanted and the colonies were stained and counted.

TABLE 1

| Cytotoxicity of 2-Halo-9-(2-Deoxy-2-Fluoro-β-D-Arabinofuranosyl)Adenines | | | | |
|---|---|---|---|---|
| | IC$_{50}$ (μM) | | | |
| Compound | L1210 | H.Ep.-2 | CCRF-CEM | K562 |
| 1g | 1.2 | 0.35 | 0.03 | 0.33 |
| 1d | 0.20 | 0.03 | 0.16 | 0.02 |
| 1b | 0.60 | 0.60 | 0.03 | — |

EXAMPLE 8

Summary of Antitumor Activity

CD2F1 mice were implanted intraperitoneally (ip) with 10$^6$ P388 leukemia cells. Tumor implantation day was designated Day 0. The compounds were administered ip at several dosage levels, ranging from toxic to non-toxic. Tumor-bearing control mice were untreated. Mice were observed for life span. Antitumor activity was assessed on the basis of percentage median increase in life span (% ILS) and net log cell kill. Calculations of net log cell kill were made from the tumor-doubling time that was determined from an internal tumor titration consisting of implants from serial 1→10 dilutions. Long-term survivors were excluded from calculations of percentage ILS and tumor cell kill. To assess tumor cell kill at the end of treatment, the survival time difference between treated and control groups was adjusted to account for regrowth of tumor cell populations that may occur between individual treatments. The results are set forth in Table 2.

TABLE 2

| Compound | Expt. | Optimal IP Dosage (≦LD$_{10}$) (mg/kg/dose) | Schedule | Median % ILS[a] (Dying Mice Only) | Tumor-Free Survivors |
|---|---|---|---|---|---|
| 1d | A | 100 | qd 1–5 | +38 | 0/5 |
| | | 50 | | +35 | 0/5 |
| | | 25 | | +31 | 0/5 |
| | B | 300 | qd 1–5 | Toxic | 0/3 |
| | | 200 | | +59 | 0/3 |
| | | 100 | | +36 | 0/3 |
| | C | 30 | q3h × 8, | Toxic | 0/6 |
| | | 20 | Days 1, 5, 9 | +220 | 1/6 |
| | | 10 | | +140 | 0/6 |
| | D | 25 | q3h × 8, | +118 | 0/5 |
| | | 17 | Days 1, 5, 9 | +113 | 0/6 |
| | | 11 | | +95 | 0/6 |
| 1g | E | 200 | qd 1–5 | Toxic | 0/3 |
| | | 100 | | +63 | 0/3 |
| | | 50 | | +58 | 0/2 |
| | D | 25 | qd3h × 8, | +81 | 0/6 |
| | | 17 | Days 1, 5, 9 | +86 | 0/6 |
| | | 11 | | +77 | 0/6 |
| 1b | F | 300 | qd 1–5 | Toxic | 0/6 |
| | | 200 | | +33 | 0/6 |
| | | 100 | | +18 | 0/6 |
| | G | 30 | qh × 8, | +100 | 0/6 |
| | | 20 | Days 1, 5, 9 | +84 | 0/6 |
| | | 10 | | +71 | 0/6 |
| | H | 50 | qh × 8, | +41 | 0/6 |

TABLE 2-continued

| Compound | Expt. | Optimal IP Dosage (≦LD₁₀) (mg/kg/dose) | Schedule | Median % ILS[a] (Dying Mice Only) | Tumor-Free Survivors |
|---|---|---|---|---|---|
| | | 40 | Days 1, 5, 9 | +41 | 0/6 |
| | | 30 | | +42 | 0/6 |
| 2nd Compound in Table 1 of U.S. Pat. No. 4,751,221 | | 200 | | Toxic | 0/6 |
| | | 100 | | +8 | 0/6 |
| | | 50 | | +11 | 0/6 |

[a]An ILS (increase in life span) of 20-74% is considered moderate activity; an ILS of ≧75% is considered good activity (NCI activity criteria for drug testing).

EXAMPLE 9

This example illustrates one of the advantages of the compounds of this invention over previous anticancer compounds, such as 2-fluoro-9-β-D-arabinofuranosyladenine, i.e., that they are not degraded by the enzyme purine nucleoside phosphorylase nearly so rapidly. Purine nucleoside phosphorylase was partially purified from Escherichia coil B (lyophilized cells) obtained from Sigma Chemical Co. The enzyme reaction mixture consisted of nucleoside substrate (0.5 mM), phosphate buffer (50 mM, pH 8.0) and enzyme in a final volume of 1.0 mL. The reaction was terminated after incubations of 30, 60, 120, 180 and 240 minutes, and the amounts of nucleoside and base present were determined by HPLC on a reversed-phase column. The results are set forth in Table 3.

TABLE 3

| Phosphorolysis of Nucleosides | |
|---|---|
| Compound | % Cleavage |
| 1b | 45 |
| 1d | 39 |
| 1g | 10 |
| 2-fluoro-9-β-D-arabinofuranosyladenine | 99 |
| 2-chloro-2'-deoxyadenosine | >99 |
| 2-fluoro-2'-deoxyadenosine | >99 |

What is claimed is:

1. A nucleoside having Formula I

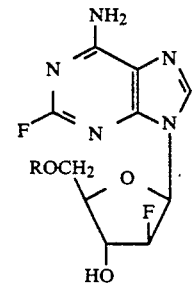

wherein R is hydrogen or acyl.

2. A nucleoside as defined in claim 1, where R is hydrogen.

* * * * *